(12) United States Patent  
Gu (10) Patent No.: US 7,629,174 B2  
(45) Date of Patent: Dec. 8, 2009

(54) ANALYTE DETECTOR

(75) Inventor: Yuandong Gu, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 776 days.

(21) Appl. No.: 11/213,526

(22) Filed: Aug. 26, 2005

(65) Prior Publication Data

US 2007/0048178 A1   Mar. 1, 2007

(51) Int. Cl.
*G01N 21/00* (2006.01)
*G01N 35/00* (2006.01)
*G01N 33/00* (2006.01)
*G01N 27/00* (2006.01)
*C12Q 1/68* (2006.01)
*B01L 3/00* (2006.01)
*G01N 33/48* (2006.01)
*G01N 27/16* (2006.01)

(52) U.S. Cl. .................. 436/164; 422/50; 422/55; 422/56; 422/57; 422/61; 422/68.1; 422/82.01; 422/82.02; 422/82.05; 422/95; 436/43; 436/91; 436/95; 436/149; 356/432

(58) Field of Classification Search .......... 422/50, 422/55, 56, 57, 61, 68.1, 82.01, 82.02, 82.05; 422/95; 436/43, 91, 95, 149, 164; 356/432
See application file for complete search history.

(56) References Cited

U.S. PATENT DOCUMENTS

| | | |
|---|---|---|
| 4,371,374 A | 2/1983 | Cerami et al. |
| 5,217,691 A | 6/1993 | Greene et al. |
| 5,244,562 A | 9/1993 | Russell |
| 5,503,770 A | 4/1996 | James et al. |
| 5,543,024 A | 8/1996 | Hanazato et al. |
| 6,063,637 A | 5/2000 | Arnold et al. |
| 6,201,980 B1 | 3/2001 | Darrow et al. |
| 6,284,197 B1 | 9/2001 | Abbott et al. |
| 6,288,392 B1 | 9/2001 | Abbott et al. |
| 6,319,540 B1 | 11/2001 | Van Antwerp et al. |
| 6,413,587 B1 | 7/2002 | Hawker et al. |
| 6,468,657 B1 | 10/2002 | Hou et al. |
| 6,475,750 B1 | 11/2002 | Han et al. |
| 6,484,045 B1 | 11/2002 | Holker et al. |
| 6,602,678 B2 | 8/2003 | Kwon et al. |
| 6,692,699 B2 | 2/2004 | Abbott et al. |

(Continued)

OTHER PUBLICATIONS

Germer et al., "Anomalous Electric Conductivity in Amphiphilic Smectic Liquid Crystals with Terminal Diol-Groups," Molecular Crystals and Liquid Crystals, vol. 331, pp. 643-650, 1999.

(Continued)

*Primary Examiner*—Jill Warden
*Assistant Examiner*—Dean Kwak
(74) *Attorney, Agent, or Firm*—Kris T. Fredrick (57) ABSTRACT

An analyte detector is disclosed. The analyte detector includes a substrate having a surface, a self-assembled monolayer comprising a plurality of molecules bonded to the surface, the molecules having a structure (I) defined herein, and a liquid crystal layer having a plurality of liquid crystal molecules aligned on a top surface of the self-assembled monolayer. The liquid crystal molecule includes a diol moiety that interacts with the molecule having a structure (I). Methods of detecting an analyte are also disclosed.

19 Claims, 5 Drawing Sheets

U.S. PATENT DOCUMENTS

| | | | |
|---|---|---|---|
| 6,780,492 | B2 | 8/2004 | Hawker et al. |
| 6,797,463 | B2 | 9/2004 | Abbott et al. |
| 6,824,837 | B2 | 11/2004 | Abbott et al. |
| 6,919,730 | B2 | 7/2005 | Cole et al. |
| 7,049,645 | B2 | 5/2006 | Sawada et al. |
| 7,368,085 | B2 | 5/2008 | Gu et al. |
| 2002/0012649 | A1 | 1/2002 | Kawada et al. |
| 2002/0164604 | A1 | 11/2002 | Abbott et al. |
| 2003/0194753 | A1 | 10/2003 | Abbott et al. |
| 2004/0038408 | A1 | 2/2004 | Abbott et al. |
| 2004/0091620 | A1 | 5/2004 | Abbott et al. |
| 2004/0161800 | A1 | 8/2004 | Abbott et al. |
| 2005/0123442 | A1* | 6/2005 | Gu et al. .................. 422/57 |
| 2005/0265914 | A1 | 12/2005 | Gu et al. |

OTHER PUBLICATIONS

Appleton et al., "Detection of Total Sugar Concentration Using Photoinduced Electron Transfer Materials: Development of Operationally Stable, Reusable Optical Sensors," Sensors and Actuators B, vol. 65, pp. 302-304, 2000.

Cary et al., "Ruthenium Bipyridine Complexes for the Recognition of Glucose," Sensors and Actuators B, vol. 87, pp. 25-32, 2002.

Chiang et al., "Study of the pH-ISFET and EnFET for Biosensor Applications," Journal of Medical and Biological Engineering, vol. 21, No. 3, pp. 135-146, 2001.

DiCesare et al., "Charge Transfer Flourescent Probes Using Boronic Acids for Monsaccharide Signaling," Journal of Biomedical Optics, vol. 7, No. 4, pp. 538-545, Oct. 2000.

Dzyadevich et al., "Application of Enzyme Field-Effect Transistors for Determination of Glucose Concentrations in Blood Serum," Biosensors & Bioelectronics, vol. 14, pp. 283-287, 1999.

Saito et al., "An ISFET Glucose Sensor with a Silicone Rubber Membrane for Undiluted Serum Monitoring," Sensors and Actuators B., vol. 20, pp. 125-129, 1994.

Shoji et al., "Poly(aniline Boronic Acid): A New Precursor to Substituted Poly(aniline)s," Langmuir, vol. 17, No. 23, 3 pages, 2001.

Shulga et al, "Overall Characterization of ISFET-based Glucose Biosensor," Sensors and Actuators B., vol. 10, pp. 41-46, 1992.

Sensors and Actuators B., vol. 76, pp. 187-192, 2001.

* cited by examiner

ANALYTE DETECTOR

BACKGROUND

The present disclosure generally relates to the field of analyte detectors, and more particularly, to analyte detectors capable of detecting polyhydroxylated compounds such as glucose.

Many different devices and methods are presently being used to measure the concentration of various sugars and amino acids in a wide variety of solutions. Many industrial manufacturing and food processing systems require that the level of one or more sugars and/or amino acids be carefully monitored at various stages to help insure the desired quality of final products. For example, the varying glucose concentrations during fermentation processes are important process control parameters, and their continuous monitoring can improve the yield and quality of the fermentation product. In addition, there are a large number of situations where the amount of sugar in finished food stuffs and other sugar containing products must be determined. On line continuous measurement is important in reducing the risk of contamination, labor costs and delays associated with off-line measurements. To be able to perform on-line measurements, there is a need for sterilizable sensors with rapid response times and high sensitivity, yet which also require minimum maintenance and calibration.

Other important uses for sugar analysis techniques is in the medical field where monitoring of sugar levels in biological fluids is desirable for the proper diagnosis and treatment of diabetes and other diseases. With respect to medical applications, glucose is by far the most important sugar, and diabetes is the most common disease for which glucose determinations are routinely conducted. Diabetes is a disease of the metabolic system that affects more than 14 million people in the United States and over 100 million people worldwide. It is characterized by an elevated blood-glucose concentration which is caused by a lack of the hormone insulin. Sugars are the primary source of metabolic energy, and the inability to self-regulate the levels of sugar metabolized by the body leads to many other medical problems, including but not limited to blindness, heart disease and kidney failure.

The one-time or 'spot' measurement of blood-glucose concentration ex vivo is also not optimal, as it requires collection of a blood sample, usually obtained by pricking the finger, which must be done at least several times each day. To avoid the need to subject the patient to this painful process for glucose monitoring, much effort has gone into identifying alternative sources for samples, such as subcutaneous tissue fluid, urine or saliva instead of blood, and for identifying less-painful and more efficient ways to obtain these samples, such as by transdermal extraction or using very thin needles. The development of new, highly sensitive and miniaturizable glucose monitoring technology may make some of these alternative methods more feasible for use at home by patients.

Treatment of diabetes often involves monitoring of the patient's blood-glucose levels, with insulin injections being given when the glucose concentration rises above normal levels. A simple and accurate method for measuring blood-glucose concentrations is an essential cornerstone of any diabetes treatment protocol, since excessively low blood-glucose levels in diabetes patients can result in coma and even death. Frequent testing and insulin administration can significantly reduce long-term complications of diabetes. The vast majority of sensors which are currently used for glucose monitoring are based on enzymes such as glucose oxidase or glucose dehydrogenase. These enzyme-based sensors are simple to use and have relatively high sensing selectivity. They are widely used for one-time measurement of blood-glucose concentrations ex vivo. However, among the drawbacks of many enzyme-based sensors are that they are costly and have a short life time. This inherently unstable enzyme must be protected from extreme conditions during manufacturing and storage in order to preserve its catalytic activity. In addition, there have been a number of problems associated with the use of enzymes in implantable sensors used in systems for continuously monitoring blood-glucose levels in vivo, among them the fact that enzymes can elicit an immune response and are not stable to most sterilization methods. The development of non-enzymatic approaches to glucose sensing is desirable in order to provide more effective management of diabetes, both for spot monitoring of glucose concentrations as well as for in vivo continuous monitoring.

A few nonenzymatic methods for measuring glucose have been proposed as alternatives to the above-described enzyme-based devices. U.S. Pat. No. 5,217,691 describes the use of boronic acids for the semiquantitative calorimetric determination of glucose. U.S. Pat. No. 4,371,374 discloses separating and quantitating glycosylated amino acids, peptides or mixtures thereof by treating a urine sample with a suitable boronic acid to complex the glycosylated compounds, separating them and analyzing the separated complexed material. U.S. Pat. No. 5,503,770 discloses a fluorescent boronic acid conjugate which emits fluorescence upon binding to saccharides. U.S. Pat. No. 5,244,562 discloses switching devices coated with a polymer imprinted with glucose and boronic acid.

Although some of the above-described sensors have shown promise, none have been found to be entirely satisfactory. There is a continuing need to develop robust sensor systems that can be used to simply, accurately, and rapidly measure the amount of a particular sugar, amino acid or related compound which is present in solutions and other environments. The need is particularly apparent with respect to ex vivo and in vivo glucose determinations which can be an important component in medical diagnosis and treatment of various metabolic disorders, including diabetes. There is also a strong need to develop robust sensor technology for real-time monitoring of sugars, amino acids and other metabolites in manufacturing process environments.

SUMMARY

The present disclosure generally relates to an analyte detector that includes a device that is capable of detecting polyhydroxylated compounds such as glucose. In one illustrative embodiment, An analyte detector is disclosed. The analyte detector includes a substrate having a surface, a self-assembled monolayer comprising a plurality of molecules bonded to the surface, the molecules having a structure (I) defined herein, and a liquid crystal layer having a plurality of liquid crystal molecules aligned on a top surface of the self-assembled monolayer. The liquid crystal molecule includes a diol moiety that interacts with the molecule having a structure (I).

In another illustrative embodiment, a method is described for detecting an analyte. The method includes the steps of contacting an analyte detector with a sample, wherein the analyte detector includes a substrate having a surface, a self-assembled monolayer comprising a plurality of molecules bonded to the metallized surface, the molecules having a structure (I) defined herein, and a liquid crystal layer having a plurality of liquid crystal molecules, aligned on a top surface of the self-assembled monolayer, the liquid crystal molecule includes a diol moiety that interacts with the molecule having a structure (I) and the liquid crystal layer having an alignment, and determining whether the alignment of the liquid crystal layer changes after the analyte detector contacts the sample.

In a further illustrative embodiment, glucose sensor for providing an output signal indicative of a glucose concentration is described. The glucose sensor includes a substrate having a surface, a self-assembled monolayer having a plurality of molecules, each molecule bonded to the surface, the molecules having a structure (I) defined herein, and a liquid crystal layer including a plurality of liquid crystal molecules, aligned on a top surface of the self-assembled monolayer, the liquid crystal molecule having a diol moiety that interacts with the molecule having a structure (I).

BRIEF DESCRIPTION OF THE DRAWINGS

The disclosure may be more completely understood in consideration of the following detailed description of the various embodiments in connection with the accompanying drawings, in which.

While the invention is amenable to various modifications and alternative forms, specifics thereof have been shown by way of example in the drawings and will be described in detail. It should be understood, however, that the intention is not to limit the invention to the particular illustrative embodiments described. On the contrary, the intention is to cover all modifications, equivalents, and alternatives falling within the spirit and scope of the invention.

DETAILED DESCRIPTION

The following description should be read with reference to the drawings, in which like elements in different drawings are numbered in like fashion. The drawings, which are not necessarily to scale, depict selected illustrative embodiments and are not intended to limit the scope of the invention. Although examples of construction, dimensions, and materials may be illustrated for the various elements, those skilled in the art will recognize that many of the examples provided have suitable alternatives that may be utilized.

The present disclosure provides an analyte detector and methods for the determination of biological levels of polyhydroxylated compounds, particularly glucose. Detection of the signal produced by the analyte detector determines the quantity of polyhydroxylated compound or analyte of interest. While the present invention is not so limited, an appreciation of various aspects of the invention will be gained through a discussion of the various illustrative embodiments and examples provided below.

As used herein, the term "alkylene" refers to a straight or branched chain divalent hydrocarbon radical optionally containing one or more heteroatomic substitutions independently selected from S, O, Si, or N. Alkylene groups generally include those with one to twenty atoms. Alkylene groups may be unsubstituted or substituted with those substituents that do not interfere with the specified function of the composition. Substituents include alkoxy, hydroxy, mercapto, amino, alkyl substituted amino, or halo, for example. Examples of "alkylene" as used herein include, but are not limited to, methylene, ethylene, propane-1,3-diyl, propane-1,2-diyl and the like.

As used herein, the term "alkenylene" refers to a straight or branched chain divalent hydrocarbon radical having one or more carbon—carbon double bonds and optionally containing one or more heteroatomic substitutions independently selected from S, O, Si, or N. Alkenylene groups generally include those with one to twenty atoms. Alkenylene groups may be unsubstituted or substituted with those substituents that do not interfere with the specified function of the composition. Substituents include alkoxy, hydroxy, mercapto, amino, alkyl substituted amino, or halo, for example. Examples of "alkenylene" as used herein include, but are not limited to, ethene-1,2-diyl, propene-1,3-diyl, and the like.

As used herein, the term "cycloalkylene" refers to an alicyclic divalent hydrocarbon radical. Cycloalkylene groups generally include those with three to twelve carbon atoms. Cycloalkylene groups may be unsubstituted or substituted with those substituents that do not interfere with the specified function of the composition. Substituents include alkoxy, hydroxy, mercapto, amino, alkyl substituted amino, or halo, for example. Such a cycloalkylene ring may be optionally fused to one or more of another heterocyclic ring(s), heteroaryl ring(s), aryl ring(s), cycloalkenyl ring(s), or cycloalkyl rings. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,2-diyl, cyclohexyl-1,3-diyl cyclohexyl-1,4-diyl, cycloheptyl-1,4-diyl, or cyclooctyl-1,5-diyl, and the like.

As used herein, the term "heterocyclylene" refers to a divalent three to twelve membered non-aromatic heterocyclic ring radical containing one or more heteroatoms independently selected from S, O, or N and having zero to five degrees of unsaturation. Heterocyclylene groups may be unsubstituted or substituted with those substituents that do not interfere with the specified function of the composition. Substituents include alkoxy, hydroxy, mercapto, amino, alkyl substituted amino, or halo, for example. Such a heterocyclylene ring may be optionally fused to one or more of another heterocyclic ring(s), heteroaryl ring(s), aryl ring(s), cycloalkenyl ring(s), or cycloalkyl rings. Examples of "heterocyclylene" as used herein include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "arylene" refers to divalent unsaturated aromatic carbocyclic radicals having a single ring, such as phenylene, or multiple condensed rings, such as naphthylene or anthrylene. Arylene groups may be unsubstituted or substituted with those substituents that do not interfere with the specified function of the composition. Substituents include alkoxy, hydroxy, mercapto, amino, alkyl substituted amino, or halo, for example. Such an "arylene" ring may be optionally fused to one or more of another heterocyclic ring(s), heteroaryl ring(s), aryl ring(s), cycloalkenyl ring(s), or cycloalkyl rings. Examples of "arylene" as used herein include, but are not limited to, benzene-1,2 diyl, benzene-1,3-diyl, benzene-1,4-diyl, naphthalene-1,8-diyl, anthracene-1,4-diyl, and the like.

As used herein, the term "heteroarylene" refers to a divalent five- to seven-membered aromatic ring radical containing one or more heteroatoms independently selected from S, O, or N. Heteroarylene groups may be unsubstituted or substituted with those substituents that do not interfere with the specified function of the composition. Substituents include alkoxy, hydroxy, mercapto, amino, alkyl substituted amino, or halo, for example. Such a "heteroarylene" ring may be optionally fused to one or more of another heterocyclic ring(s), heteroaryl ring(s), aryl ring(s), cycloalkenyl ring(s), or cycloalkyl rings. Examples of "heteroarylene" used herein include, but are not limited to, furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine 2,5-diyl, pyrimidine-2,4-diyl, quinoline-2,3-diyl, and the like.

Figure 1:
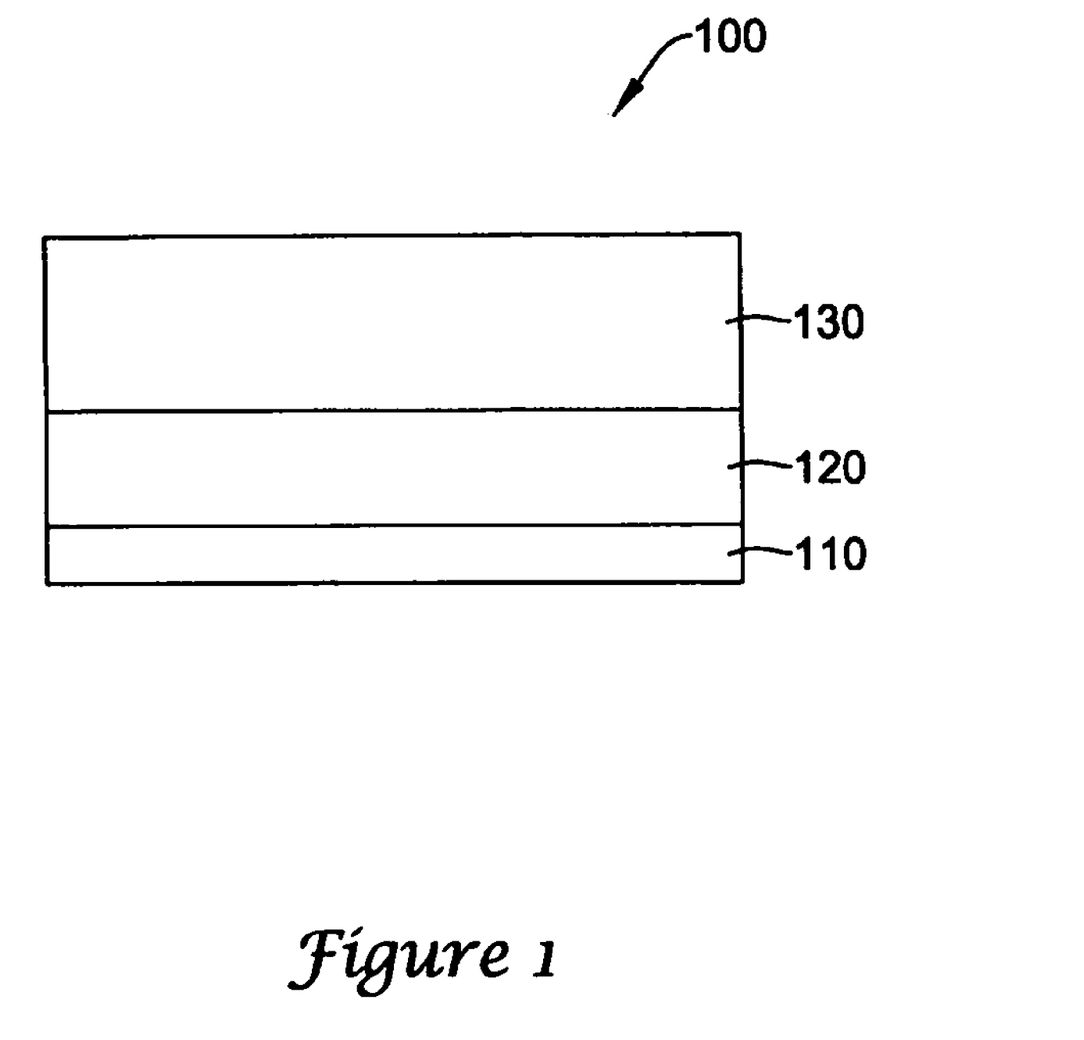
FIG. 1 is a schematic cross-sectional view of an illustrative analyte detector.

FIG. 1 is a schematic cross-sectional view of an illustrative analyte detector 100. The illustrated analyte detector 100 can include a substrate 110, a self-assembled monolayer 120 disposed on the substrate 110 and a liquid crystal layer 130 disposed on the self-assembled monolayer 120. The liquid crystal layer 130 can include a plurality of liquid crystal molecules aligned on a top surface of the self-assembled monolayer 120. In many embodiments, the liquid crystal molecules include a diol moiety that interacts with molecules that make up the self-assembled monolayer 120, as further described below.

The term "substrate" refers to a solid object or surface upon which another material is layered or attached. Solid supports include, but are not limited to, glass, metals, gels, and filter paper, among others. The substrate 110 can be formed of any useful material. Illustrative useful substrates 110 can be rigid or flexible and can be optically transparent or optically opaque, depending on the application. Substrate 110 can be an electrical insulator, conductor or semiconductor. Some suitable substrate materials include, but are not limited to, inorganic crystals, inorganic glasses, inorganic oxides, metals, organic polymers and combinations thereof. In some embodiments, a layer of metal can be disposed on the substrate to form a "metallized surface," if desired.

When so provided, the metal can be deposited onto the substrate by any method including, but not limited to, evaporative deposition, sputtering, electroless deposition, electrolytic deposition and adsorption or deposition of preform particles of the metal including metallic nanoparticles. In some embodiments, the metal layer may include, but is not limited to, gold, silver, platinum, palladium, nickel and/or copper. In one embodiment, more than one metal is used. The more than one metal can be present as an alloy or formed into a layered "sandwich" structure, or laterally adjacent to one another. In a particular illustrative embodiment, the metal used for the substrate is gold.

A self-assembled monolayer (SAM) 120 is generally depicted as an assembly of organized, closely packed linear molecules. In the illustrative embodiment, the self-assembled monolayer 120 includes a plurality of molecules bonded to the substrate 110 at a first end of the molecule and an opposing second end of the molecule can bond with a liquid crystal layer 130 molecules and is also able to form a stable anionic complex with a polyhydroxylated compound, such as, glucose.

In an illustrative embodiment, the plurality of molecules capable of forming a stable anionic complex with a polyhydroxylated compound can have a structure (I):

where, R is a ligand bonded to the substrate surface, $R_1$ is a $(C_{10}\text{-}C_{24})$ alkylene, or $(C_{10}\text{-}C_{24})$ alkenylene, and $R_2$ is an $(C_3\text{-}C_{14})$ cycloalkylene, $(C_3\text{-}C_{14})$ heterocyclylene, $(C_3\text{-}C_{24})$ arylene, or $(C_3\text{-}C_{14})$ heteroarylene. In one embodiment $R_1$ is a $(C_{10}\text{-}C_{20})$ alkylene. In another embodiment, $R_2$ is a phenylene or naphthalene.

The ligand R can be covalently bonded to the surface of the substrate 110. As noted above, the surface of the substrate 110 can be a metallized surface. The ligand can be capable of bonding the molecule of structure (I) to a variety of inorganic materials such as, for example, gold, silver, copper, lead, tantalum oxide, silicon oxide, zirconium oxide, tin oxide, or group III-IV semiconductors, or mixtures thereof. In some embodiments, the ligand can be a thiol, siloxane, or phosphate. For example, a thiol ligand can bond to conductive metals such as, for example, gold, silver or copper. A siloxane ligand can bond, for example, to silicon oxide or glass. A phosphate or phosphonate ligand can bond, for example, to tantalum oxide, zirconium oxide or tin oxide. Thus, the ligand can be selected, depending on the material forming the surface of the substrate 110.

Illustrative embodiments of the SAM molecule of structure (I) include:

-continued

The boronic acid moiety can be in the ortho, meta, or para position on the phenyl ring for any of the compounds shown above.

The SAM molecules having structure (I) are capable of forming a stable anionic complex with a polyhydroxylated compound such as, for example, glucose. An illustrative glucose binding mechanism for molecules having structure (I) is described as:

Although not being bound by any particular theory, it is believed that the mechanism of boronic acid's moiety polyol sensitivity is that the anionic form of the boronic acid moiety can form covalent complexes with molecules having diol groups held in a coplanar configuration, such as a cis-2 diol or cis-3 diol molecule, for example, glucose. Binding of the diol to the anionic boronic acid moiety stabilizes the anionic boronic acid moiety. The net outcome of this reversible binding between glucose and the anionic boronic acid moiety is the increase of the fraction of negatively charged boronic acid.

As used herein, the term "liquid crystal" refers to a thermodynamic stable phase characterized by anisotropy of properties without the existence of a three-dimensional crystal lattice, generally lying in the temperature range between the solid and isotropic liquid phase. As used herein, the term "mesogen" refers to compounds that form liquid crystals, and in particular rigid rodlike or disclike molecules which are components of liquid crystalline materials. As used herein, "thermotropic liquid crystal" refers to liquid crystals which result from the melting of mesogenic solids due to an increase in temperature. Both pure substances and mixtures form thermotropic liquid crystals. "Lyotropic," as used herein, refers to molecules which form phases with orientational and/or positional order in a solvent. Lyotropic liquid crystals can be formed using amphiphilic molecules (e.g., sodium laurate, phosphatidylethanolamine, lecithin). The solvent can be water.

Any compound or mixture of compounds that forms a mesogenic layer and include a terminal diol moiety can be used in the liquid crystal layer described herein. The mesogens can form thermotropic or lyotropic liquid crystals. The mesogenic layer can be either continuous or it can be patterned. Both the thermotropic and lyotropic liquid crystals can exist in a number of forms including nematic, chiral nematic, smectic, polar smectic, chiral smectic, frustrated phases and discotic phases. The terminal diol moiety can form a stable anionic complex with the opposing second end of the SAM 120 layer as shown in FIG. 2.

Example of useful liquid crystal compounds that include a terminal diol moiety include compounds described in US 2002/0012649 and "Anomalous Electric Conductivity in Amphiphilic Smectic Liquid Crystals with Terminal Diol-groups", R. Germer et al., Molecular Crystals and Liquid Crystals 331, 643-650 (1999), both of which are incorporated by reference herein.

Figure 2:
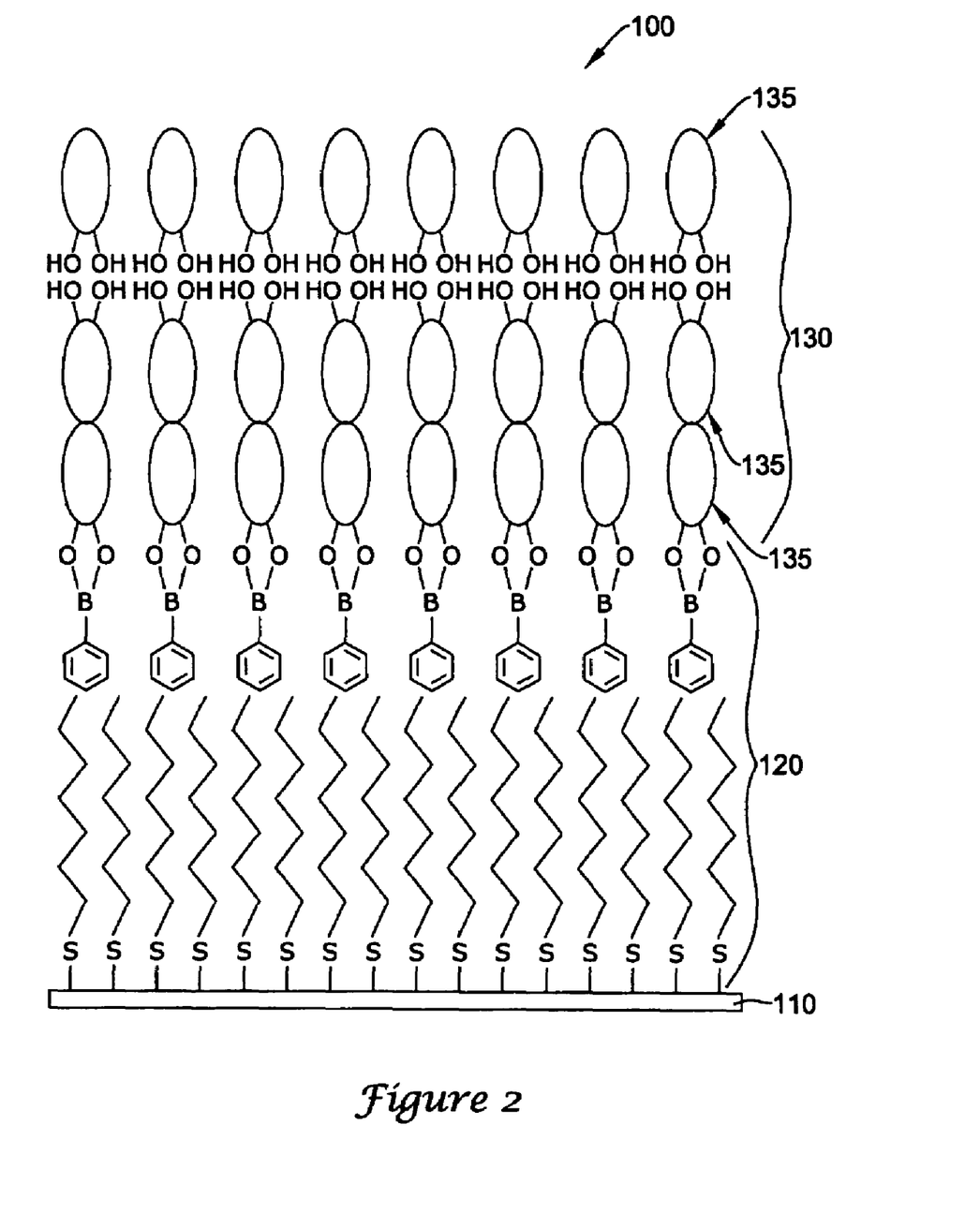
FIG. 2 is a schematic view of an illustrative analyte detector contacting a sample having a low concentration of glucose.
Figure 3:
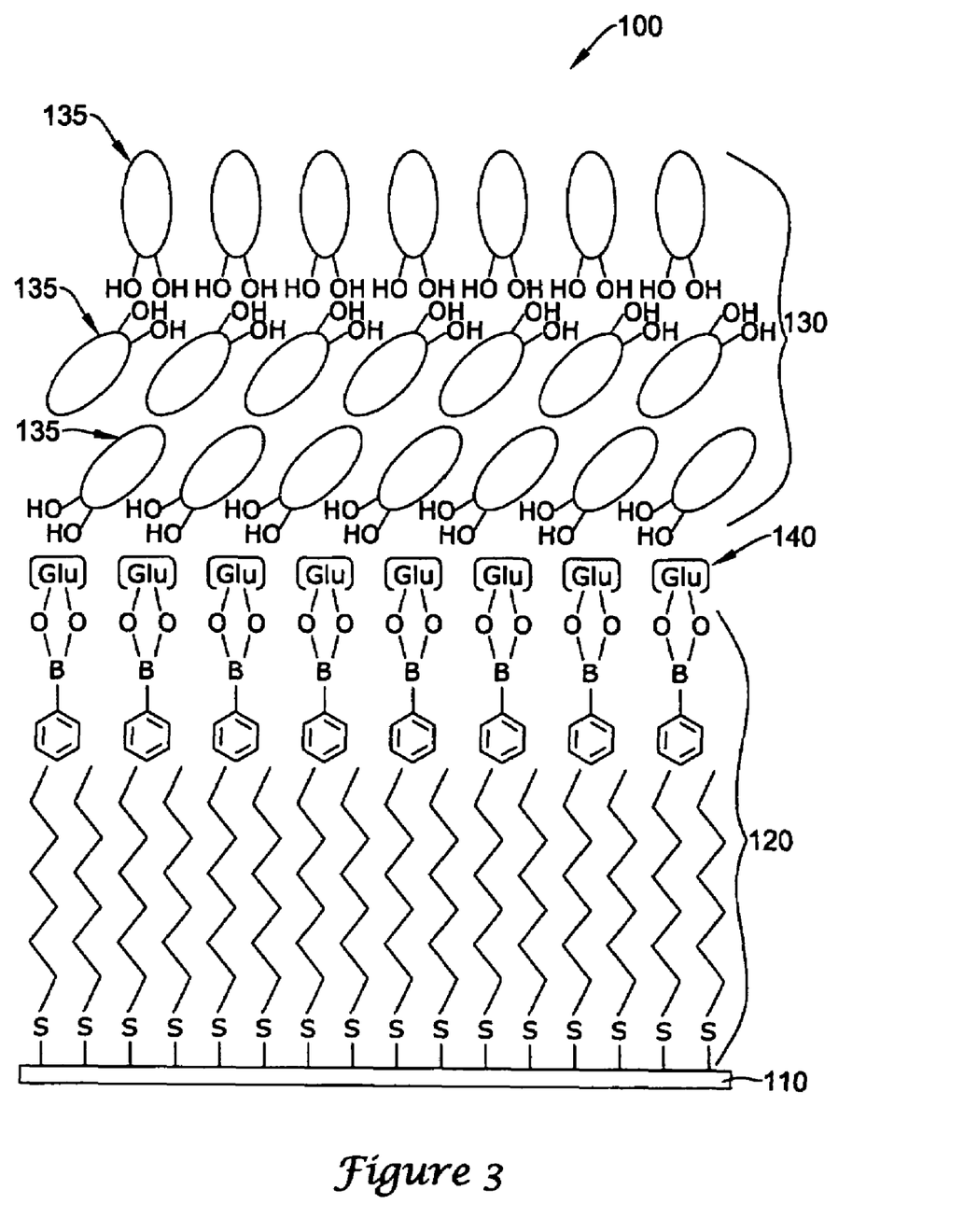
FIG. 3 is a schematic view of an illustrative analyte detector contacting a sample having a high concentration of glucose.

FIG. 2 is a schematic view of an illustrative analyte detector 100 contacting a sample having a low concentration of glucose. FIG. 3 is a schematic view of an illustrative analyte detector 100 contacting a sample having a high concentration of glucose. In the illustrated embodiment, a self-assembled monolayer 120 (SAM) is disposed between a substrate 110 and a liquid crystal layer 130. The illustrative liquid crystal layer 130 includes a plurality of molecules having one or more mesogens 130.

At low concentrations of glucose, the liquid crystal layer 130 is ordered as shown in FIG. 2. Increasing the concentration of glucose 140 in the sample contacting the analyte detector 100 causes the liquid crystal to become disordered. The amount of disorder in the liquid crystal layer 130 can indicate the concentration of glucose 135 present in the sample contacting the analyte detector 100. Reducing the concentration of glucose 135 in the sample allows the liquid crystal layer 130 to increase in order.

Although many changes in the liquid crystal layer 130 can be detected by visual observation under ambient light, any means for detecting the change in the liquid crystal layer 130 can be incorporated into, or used in conjunction with, the detector 100. Thus, it is within the scope of the present disclosure to use lights, microscopes, spectrometry, electrical techniques and the like to aid in the detection of a change in the liquid crystal layer 130.

Some illustrative embodiments utilize light in the visible region of the spectrum to detect a change in the liquid crystal layer 130. The light can be used to simply illuminate details of the liquid crystal layer 130. Alternatively or in addition, the light can be passed through the liquid crystal layer 130 and the amount of light transmitted, absorbed and/or reflected can be measured. Light in the ultraviolet, infrared, and/or other regions can also be used.

Figure 4:
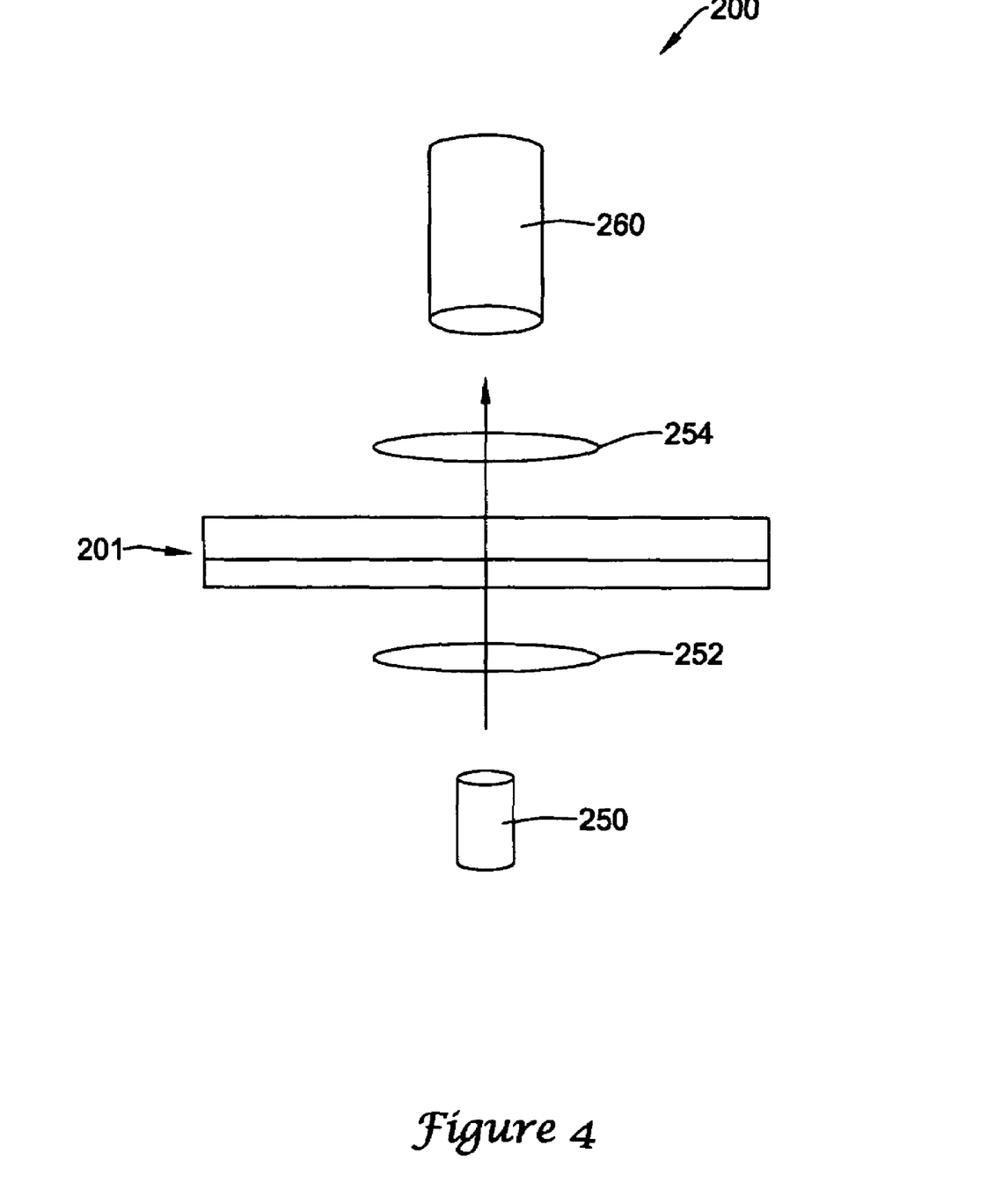
FIG. 4 is a schematic diagram of an illustrative analyte detector system.

In one illustrative embodiment, and as shown in FIG. 4, the quantification of light transmission through the liquid crystal layer 130 can be preformed based on quantification of transmitted and/or reflected light. Light can be transmitted from a light source 250 and light transmitted through the liquid crystal layer can be detected by a light detector 260.

The present disclosure is not limited to any particular mechanism of action. Indeed, an understanding of the mechanism of action is not required to practice the present invention. Nevertheless, it is contemplated that the self assembled monolayer imparts order to thin films of liquid crystal placed onto their surface. These ordered films of liquid crystal may preserve the plane of polarized light passing through them. If the liquid crystal possesses a well-defined distortion—such as a 90 degree twist distortion—then the liquid crystal will change the polarization of the transmitted light in a well-defined and predictable manner. It is further contemplated that ordered films of liquid crystal may differentially absorb (relative to randomly ordered films of liquid crystal) specific wavelengths of light.

In some embodiments, the amount of glucose bound to the self assembled monolayer increases with the concentration/amount of glucose present in a sample in contact with an analyte detector. In one embodiment, the amount of bound glucose changes the degree of disorder introduced into a thin film of liquid crystal that is ordered by nature of the underlying self assembled monolayer. In some embodiments, the degree of order present in a thin film of liquid crystal determines the amount of light transmitted through the film when viewed through crossed polarizers. In other embodiments (see FIG. 5), the degree of order present in a thin film of liquid crystal determines the amount of light transmitted through the film when viewed using specific wavelengths of light. In still other embodiments, the reflectivity of an interface to a liquid crystal can change with the orientation of the liquid crystal. Therefore, in some embodiments, oblique illumination of the analyte detector is utilized with collection and analysis of reflected light being performed.

Accordingly, and in some embodiments, a plate reader system may be used to detect light transmission through an analyte detector when viewed through cross polarizers. The transmission of light through a liquid crystal assay device illuminated with a suitable wavelength of light, or reflection of light (i.e., polarized light or non-polarized light of specific wavelengths) from the surface of an analyte detector.

Figure 5:
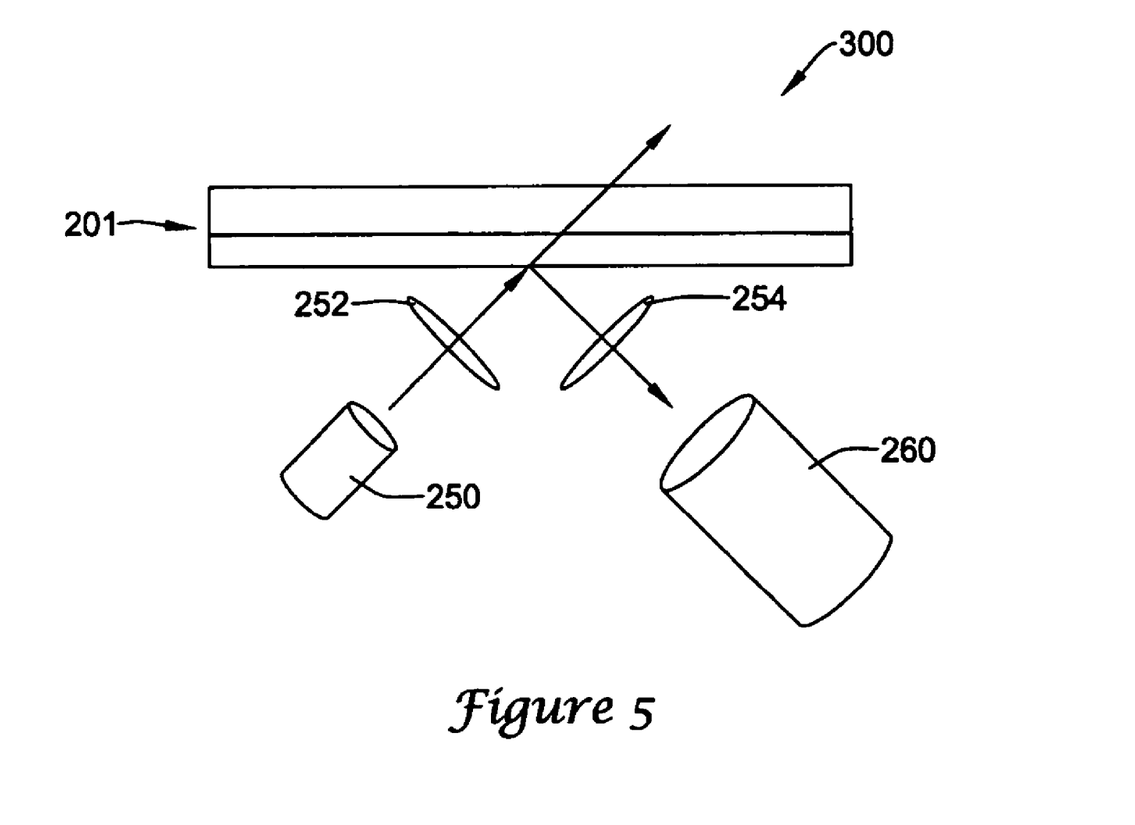
FIG. 5 is a schematic diagram of another illustrative analyte detector system.

Non-limiting examples of the plate reader systems 200, 300 are provided in FIG. 4 and FIG. 5. In illustrative embodiments, two polarizing filters 252, 254 are placed in the optical pathway of the analyte detector 201 in a crossed or parallel polar configuration. One filter 252 is placed on the emission or light source 250 side of the light path prior to passing through the sample while a second polarizing filter 254 is placed on the analyzing side of the light path after light has passed through the sample but before it is collected by a sensing or detecting device 260 such as, for example, a photodiode or a CCD. An ordered liquid crystal in the analyte detector 201 preserves the plane of polarization and the amount of light reaching the light gathering and sensing device 260 is markedly attenuated when viewed through cross polarizers or markedly accentuated when viewed through parallel polarizers. Random organization of the liquid crystal of the analyte detector 201 does not preserve the plane of polarization and the amount of light passing through crossed polarizers, reaching the light collecting and sensing device 260 is relatively unaffected. Accordingly, in some embodiments, the binding of glucose by the self assembled monolayer introduces disorder into the overlying liquid crystal layer that increases with the amount of bound glucose. In other embodiments, specific bandpass filters 252, 254 are placed on the emission 250 side of the light path before the light encounters the sample 201 as well as on the collection side of the light path (after light has passed through or is reflected by the sample but before reaching the light collecting and sensing device 260 (e.g., photodiode or CCD). This configuration is useful for quantifying both reflected and transmitted light.

EXAMPLES

All of the starting materials described herein are commercially available from a variety of sources such as, Aldrich Chemical (Milwaukee, Wis.) or readily synthesized using conventional methods. Illustrative molecules that are suitable for forming a monolayer on a device surface are synthesized below. A variety of additional molecules can be synthesized using the scheme below by varying the starting materials as is known. Two illustrative thiols and two illustrative phosphates are described below.

Thiol Molecules

A four inch silicon wafer with a layer of $SiO_2$ on top, is cleaned with hot piranha bath (110° C.), cleaned with DI water, and baked at 110° C. for 1 minute.

A portion of the silicon wafer is then coated with a 100 Å titanium layer and then a 1000 Å gold layer is deposited on the titanium layer using known deposition techniques.

The silicon wafer is then diced into 1 cm×5 cm pieces with half of each die covered with titanium/gold and half of it is bare silicon.

The titanium/gold coated silicon pieces are soaked in a diluted boiling piranha solution (1:4 $H_2O_2/H_2SO_4$) for 1 minute. The titanium/gold coated silicon pieces are then rinsed thoroughly with water, $H_2O_2$, water, and then dried in a jet of $N_2$.

The dried titanium/gold coated silicon pieces are dipped in 1 mM thiolated phenylboronic acid (see thiol molecules above) solutions (deoxygenated with $N_2$ or Ar) at room temperature avoiding light.

The thiol molecules attach to the gold layer and form a monolayer of molecules. A layer of thiol terminated liquid crystals can be disposed on the monolayer of molecules to form a glucose detector.

The present invention should not be considered limited to the particular examples described above, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

What is claimed is:

1. An analyte detector comprising:

a substrate having a surface;

a self-assembled monolayer comprising a plurality of molecules bonded to the surface, the molecules having a structure (I):

wherein,

R is a ligand bonded to the surface of the device;

$R_1$ is a ($C_{10}$-$C_{24}$) alkylene, or ($C_{10}$-$C_{24}$) alkenylene;

$R_2$ is an ($C_3$-$C_{14}$) cycloalkylene, ($C_3$-$C_{14}$) heterocyclylene, ($C_3$-$C_{24}$) arylene, or ($C_3$-$C_{14}$) heteroarylene; and a liquid crystal layer comprising a plurality of liquid crystal molecules, aligned on a top surface of the self-assembled monolayer, the liquid crystal molecule comprising a diol moiety that interacts with the molecule having a structure (I).

2. An analyte detector according to claim 1 wherein $R_1$ is a ($C_{10}$-$C_{20}$) alkylene.

3. An analyte detector according to claim 1 wherein $R_2$ is a phenylene or naphthalene.

4. An analyte detector according to claim 1 wherein the ligand is a thiol, phosphate, or siloxane.

5. An analyte detector according to claim 1 wherein the ligand is a thiol, $R_1$ is a ($C_{10}$-$C_{20}$) alkylene, and $R_2$ is a phenylene.

6. An analyte detector according to claim 1 wherein the liquid crystal molecule comprises a terminal diol moiety that interacts with the molecule having a structure (I).

7. An analyte detector according to claim 1 further comprising a light source transmitting light through the liquid crystal layer and a light detector receiving light transmitted through the liquid layer.

8. An analyte detector according to claim 7 further comprising a light polarizer disposed between the light source and the liquid crystal layer.

9. An analyte detector according to claim 7 further comprising a light polarizer disposed between the liquid crystal layer and the light detector.

10. A method of detecting an analyte comprising the steps of:

contacting an analyte detector with a sample, wherein the analyte detector comprises:

a substrate having a surface;

a self-assembled monolayer comprising a plurality of molecules bonded to the metallized surface, the molecules having a structure (I):

wherein,

R is a ligand bonded to the surface of the device;

$R_1$ is a ($C_{10}$-$C_{24}$) alkylene, or ($C_{10}$-$C_{24}$) alkenylene;

$R_2$ is an ($C_3$-$C_{14}$) cycloalkylene, ($C_3$-$C_{14}$) heterocyclylene, ($C_3$-$C_{24}$) arylene, or ($C_3$-$C_{14}$) heteroarylene; and a liquid crystal layer comprising a plurality of liquid crystal molecules, aligned on a top surface of the self-assembled monolayer, the liquid crystal molecule comprising a diol moiety that interacts with the molecule having a structure (I) and the liquid crystal layer having an alignment; and determining whether the alignment of the liquid crystal layer changes after the analyte detector contacts the sample.

11. A method according to claim 10 wherein the contacting step comprises contacting an analyte detector with a sample comprising glucose to induce a change in the alignment of the liquid crystal layer.

12. A method according to claim 10 wherein the determining step comprises illuminating the liquid crystal layer with light to determine the degree of disorder introduced into the liquid crystal layer after the analyte detector contacts the sample.

13. A method according to claim 10 wherein the contacting step comprises contacting an analyte detector with a sample, the analyte detector comprises: a substrate having a surface; a self-assembled monolayer comprising a plurality of molecules, each molecule bonded to the surface, the molecules having a structure (I):

wherein, R is a thiol bonded to the surface of the device; $R_1$ is a ($C_{10}$-$C_{20}$) alkylene; and $R_2$ is a phenylene.

14. A method according to claim 10 wherein the determining step comprises transmitting light from a light source through the liquid crystal layer and detecting light transmitted through the liquid crystal layer with a light detector to determine the degree of disorder introduced into the liquid crystal layer after the analyte detector contacts the sample.

15. A glucose sensor for providing an output signal indicative of a glucose concentration, the glucose sensor comprising:

a substrate having a surface;

a self-assembled monolayer comprising a plurality of molecules, each molecule bonded to the surface, the molecules having a structure (I):

wherein,

R is a ligand bonded to the surface of the device;

$R_1$ is a ($C_{10}$-$C_{24}$) alkylene, or ($C_{10}$-$C_{24}$) alkenylene;

$R_2$ is an ($C_3$-$C_{14}$) cycloalkylene, ($C_3$-$C_{14}$) heterocyclylene, ($C_3$-$C_{24}$) arylene, or ($C_3$-$C_{14}$) heteroarylene; and a liquid crystal layer comprising a plurality of liquid crystal molecules, aligned on a top surface of the self-assembled monolayer, the liquid crystal molecule comprising a diol moiety that interacts with the molecule having a structure (I).

16. A glucose sensor according to claim 15 wherein the ligand is a thiol, $R_1$ is a ($C_{10}$-$C_{20}$) alkylene, and $R_2$ is a phenylene.

17. A glucose sensor according to claim 15 wherein the liquid crystal comprises a terminal diol moiety that interacts with the molecule having a structure (I).

18. A glucose sensor according to claim 15 further comprising a light source transmitting light through the liquid crystal layer and a light detector receiving light transmitted through the liquid crystal layer.

19. A glucose sensor according to claim 18 further comprising a first light polarizer disposed between the light source and the liquid crystal layer and a second light polarizer disposed between the liquid crystal layer and the light detector.

* * * * *

UNITED STATES PATENT AND TRADEMARK OFFICE
CERTIFICATE OF CORRECTION

PATENT NO. : 7,629,174 B2
APPLICATION NO. : 11/213526
DATED : December 8, 2009
INVENTOR(S) : Yuandong Gu It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1139 days.

Signed and Sealed this

Second Day of November, 2010

David J. Kappos
*Director of the United States Patent and Trademark Office*